United States Patent
Azemoto et al.

(10) Patent No.: US 8,559,686 B2
(45) Date of Patent: Oct. 15, 2013

(54) MEDICAL IMAGE DATA ALIGNMENT APPARATUS, METHOD AND PROGRAM

(75) Inventors: Shogo Azemoto, Tokyo (JP); Yasuaki Goko, Tokyo (JP); Masakatsu Hoashi, Tokyo (JP)

(73) Assignee: AZE Ltd., Tokyo (JP)

( * ) Notice: Subject to any disclaimer, the term of this patent is extended or adjusted under 35 U.S.C. 154(b) by 543 days.

(21) Appl. No.: 12/875,452

(22) Filed: Sep. 3, 2010

(65) Prior Publication Data

US 2011/0069873 A1  Mar. 24, 2011

(30) Foreign Application Priority Data

Sep. 24, 2009  (JP) ................................ 2009-218831

(51) Int. Cl.
*G06K 9/00* (2006.01)

(52) U.S. Cl.
USPC ........................................................ 382/128

(58) Field of Classification Search
USPC .......... 382/128–132, 278, 293, 294; 607/116; 600/429, 407
See application file for complete search history.

(56) References Cited

U.S. PATENT DOCUMENTS

| | | | |
|---|---|---|---|
| 6,266,453 B1* | 7/2001 | Hibbard et al. | 382/294 |
| 7,822,291 B2* | 10/2010 | Guetter et al. | 382/294 |
| 8,108,204 B2* | 1/2012 | Gabrilovich et al. | 704/9 |
| 2010/0284598 A1* | 11/2010 | Zhao et al. | 382/131 |

FOREIGN PATENT DOCUMENTS

JP  A-10-137231  5/1998

OTHER PUBLICATIONS

Rispler, S. et al.; Abstract of "Integrated Single-Photon Emission Computed Tomography and Computed Tomography Coronary Angiography for the Assessment of Hemodynamically Significant Coronary Artery Lesions," *Journal of the American College of Cardiology*, 2007, pp. 1059-1067, vol. 49, No. 10.
Aladl, U. et al.; Abstract of "Automated Image Registration of Gated Cardiac Single-Photon Emission Computed Tomography and Magnetic Resonance Imaging," *Journal of Magnetic Resonance Imaging*, Mar. 2004, pp. 283-290, vol. 19, No. 3.
Nakajo, H. et al., "Three-dimensional Registration of Myocardial Perfusion SPECT and CT Coronary Angiography," *Annals of Nuclear Medicine*, 2005, pp. 207-215, vol. 19, No. 3.

* cited by examiner

*Primary Examiner* — Claire X Wang
(74) *Attorney, Agent, or Firm* — Oliff & Berridge, PLC (57) ABSTRACT

An object of the present invention is to provide a medical image data alignment apparatus, method and program capable of aligning different kinds of image data on a tissue to be objected at high precision and in a short time. According to the present invention, a patient SPECT and a patient CT are aligned via atlas data. The atlas data is a standard of SPECT image data, and is created based on SPECT image data of a plurality of patients. The patient SPECT and the atlas data are aligned based on the correlation of image signal values thereof, and a first transformation matrix $T_1$ is determined. The atlas data and the patient CT are aligned based on the coordinate information added to these data in advance, and a second transformation matrix $T_2$ is determined. The patient SPECT and the patient CT are aligned using the first transformation matrix $T_1$ and the second transformation matrix $T_2$.

9 Claims, 5 Drawing Sheets

PATIENT SPECT

ATLAS DATA

FIG. 7

ATLAS DATA

PATIENT CT

FIG. 8

MEDICAL IMAGE DATA ALIGNMENT APPARATUS, METHOD AND PROGRAM

RELATED APPLICATIONS

This application claims the priority of Japanese Patent Application No. 2009-218831 filed on Sep. 24, 2009, which is incorporated herein by reference.

BACKGROUND OF THE INVENTION

1. Field of the Invention

The present invention relates to a technology for aligning, among a plurality of medical images, image data on a tissue to be objected to be an object of diagnosis and observation, including such organs as a heart, liver, pancreas, kidney, spleen, brain and lung, or such biotissue as a tumor (coordinating, among the images, each image point corresponding to each portion of a tissue to be objected in each image), and more particularly to a medical image data alignment apparatus, method and program for aligning different kinds of image data on a tissue to be objected, between a medical image obtained by an image diagnostic apparatus (hereafter called "first kind image diagnostic apparatus") capable of generating an image of anatomical form information on the tissue to be objected, such as an X-ray CT (Computed Tomography) apparatus and MRI (Magnetic Resonance Imaging) apparatus and a medical image obtained by an image diagnostic apparatus (hereafter called "second kind image diagnostic apparatus") capable of generating an image of function information including blood flow, for example, in a tissue to be objected, such as a SPECT (Single-Photon Emission Computed Tomography) apparatus.

2. Description of the Prior Art

Photographing a tissue to be objected using a CT apparatus and an MRI apparatus (first kind image diagnostic apparatus), which can generate an image of an anatomical form information on the tissue to be objected without involving a surgical procedure, is widely used in clinical fields in order to detect a structural alteration, functional disorder and presence of a pathologically altered portion of a tissue to be objected.

In particular, the image diagnosis by the X-ray CT apparatus, of which performance has advanced recently, exhibits high performance in detecting blood vessels responsible for supplying nutrition to cardiac muscles in an ischemic state (mainly coronary arteries which cause stricture by arteriosclerosis and plaque), which is critical for diagnosing ischemic heart diseases represented by cardiac infarction, is receiving attention as a method which has little effect on and imposes little stress on a patient. However a stricture of coronary artery does not always cause immediate ischemia, so diagnosis by CT image alone increases the number of false positives.

To solve this problem, a method for using the SPECT image obtained by a SPECT apparatus (second kind image diagnostic apparatus) which can generate an image of function information, such as blood flow, in addition to a CT image, so as to use an integrated image of these two medical images for diagnosis, is drawing attention. According to a diagnosis based on this integrated image, major improvements can be made in decreasing the number of false positives, compared with diagnosis based on a CT image alone (see Non-patent Document 1 listed below).

Generally in the case of integrating different kinds of medical images, such as a CT image and a SPECT image, these respective image data must be aligned, and this alignment is often manually performed by a specialist or the like. However the information to be generated into an image is different and therefore correlation is low between a CT image and a SPECT image, and the resolution of the SPECT image is low, so even if the physician has extensive experience in image diagnosis, it takes a long time to perform alignment with sufficient accuracy and reproducibility.

Therefore various methods for automatically aligning each image data of different kinds of medical images using a computer have been proposed (see Non-Patent Documents 2 and 3 listed below, and Japanese Patent Application Laid-open No. H10-137231).

According to the method in Non-patent Document 2, the left ventricle of a heart in an MR image obtained by an MRI apparatus is segmented by a threshold base method, and the left ventricle of the segmented MR image and a SPECT image are automatically aligned using a mutual information amount and a rigid transformation (rigid registration).

According to the method in Non-patent Document 3, a left ventricle model is constructed by segmenting a left ventricle in a CT image obtained by a CT apparatus, and this left ventricle model and SPECT image are automatically aligned by each method of the rigid transformation and non-rigid transformation (non-rigid registration), and also is manually aligned to verify the accuracy of the automatic alignment.

According to the method in Japanese Patent Application Laid-open No. H10-137231, image data on a brain in a CT image and image data on the brain in a SPECT image are aligned based on a conformity of the surface form of a skull in the CT image and the surface form of the skull in the SPECT image.

[Non-Patent Document 1]

Shmuel Rispler, Zohar Keidar, Eduard Ghersin, Ariel Roguin, Adrian Soil, Robert Dragu, Diana Litmanavich, Alex Frenkel, Doran Aronson, Ahuva Engel, Rafael Beyar and Ora Israel: "Integrated Single-Photon Emission Computed Tomography and Computed Tomography Coronary Angiography for the Assessment of Hemodynamically Significant Coronary Artery Lesions," Journal of the American College of Cardiology, Vol. 49, No. 10, pp. 1059-1067, 2007

[Non-Patent Document 2]

Usaf E. Alsdl, Gilbert A. Hurwitz, Damini Dey, David Levin, Maria Dragova and Piotr J. Slomka: "Automated Image Registration of Gated Cardiac Single-Photon Emission Computed Tomography and Magnetic Resonance Imaging," Journal of Magnetic Resonance Imaging, Vol. 19, No. 3, pp. 283-290, 2004

[Non-Patent Document 3]

Hidenobu Nakajo, Shin-ichiro Kumita, Keiichi Cho, and Tatsuo Kumazaki: "Three-dimensional registration of myocardial perfusion SPECT and CT coronary angiography", Annals of Nuclear Medicine, Vol. 19, No. 3, pp. 207-215, 2005

The methods according to the Non-patent Documents 2 and 3 mentioned above perform stable alignment by extracting the left ventricle portion, of which correlation with the SPECT image is relatively high, from the CT image or MRI image, and using this portion for alignment, but alignment accuracy greatly depends on the result of segmenting the left ventricle, so a problem is that the alignment accuracy falls considerably unless a good segmentation result is obtained.

The method according to Japanese Patent Application Laid-open No. H10-137231 mentioned above, on the other hand, must extract some anatomical form information from the SPECT image of which resolution is low, so this method is effective if an area of which form information can be extracted relatively easily, like the case of a skull, is imaged, but the problem is that it takes an enormous amount of time to extract the form information from the SPECT image if such an appropriate area does not exist.

SUMMARY OF THE INVENTION

With the foregoing in view, it is an object of the present invention to provide a medical image data alignment apparatus, method and program which can align different kinds of image data on a tissue to be objected, between a medical image obtained by a first kind image diagnostic apparatus which can generate an image of form information on a tissue to be objected and a medical image obtained by a second kind image diagnostic apparatus which can generate an image of function information on the tissue to be objected, with sufficient accuracy and reproducibility, in a short time.

To achieve the above object, a medical image data alignment apparatus according to the present invention is a medical image data alignment apparatus for aligning specified first medical image data holding form information of a tissue to be objected of a specified subject, obtained by a first kind image diagnostic apparatus, and specified second medical image data holding function information of the tissue to be objected of the specified subject, obtained by a second kind image diagnostic apparatus, comprising:

medical image data storage means for storing the specified first medical image data, the specified second medical image data, and atlas second medical image data which is created based on a plurality of second medical image data holding function information of tissues to be objected of a plurality of standard subjects respectively, obtained by the second kind image diagnostic apparatus, which is created so as to be a standard of the second medical image data, and to which second coordinate information to be an index of the alignment is added;

first coordinate information addition means for adding first coordinate information to be an index for alignment to the specified first medical image data;

first transformation matrix acquisition means for determining a relative positional relationship between a coordinate system to which the specified second medical image data belongs and a coordinate system to which the atlas second medical image data belongs based on the con-elation of mutual image signal values of the specified second medical image data and the atlas second medical image data, and for determining, based on the relative positional relationship, a first transformation matrix for transforming one image data out of the specified second medical image data and the atlas second medical image data into the image data in the coordinate system to which the other image data belongs;

second transformation matrix acquisition means for determining a relative positional relationship between the coordinate system to which the atlas second medical image data belongs the coordinate system to which the specified first medical image data belongs based on the first coordinate information and the second coordinate information, and for determining, based on the relative positional relationship, a second transformation matrix for transforming one image data out of the atlas second medical image data and the specified first medical image data into the image data in the coordinate system to which the other image data belongs; and specified medical image data alignment means for aligning the specified first medical image data and the specified second medical image data using the first transformation matrix and the second transformation matrix.

In the medical image data alignment apparatus according to the present invention, it is preferable that the atlas second medical image data is created by mutually aligning the plurality of second medical image data based on the correlation of respective image signal values thereof and averaging the image signal values in portions which are overlapped with each other by the alignment.

It is preferable that the first coordinate information and the second coordinate information are constituted by unit vectors in a long axis direction and a short axis direction of the specified tissue to be objected, a basic point position of the specified tissue to be objected, and a predetermined length of the specified tissue to be objected.

It is preferable that the first kind image diagnostic apparatus is a CT apparatus or an MRI apparatus, and the second kind image diagnostic apparatus is a SPECT apparatus.

The present invention can be applied to tissues to be objected, including such organs as heart, liver, pancreas, kidney, spleen, brain and lung, or such biotissue as a tumor, but it is particularly preferable that the tissue to be objected is the heart.

A medical image data alignment method according to the present invention is a medical image data alignment method for aligning specified first medical image data holding form information of a tissue to be objected of a specified subject, obtained by a first and image diagnostic apparatus, and specified second medical image data holding function information of the tissue to be objected of the specified subject, obtained by a second kind image diagnostic apparatus, comprising:

a first coordinate information addition step of adding first coordinate information to be an index for alignment to the specified first medical image data;

a first transformation matrix acquisition step of determining a relative positional relationship between a coordinate system to which the specified second medical image data belongs and a coordinate system to which atlas second medical image data belongs based on the correlation of mutual image signal values of the specified second medical image data and the atlas second medical image data which is created based on a plurality of second medical image data holding function information of tissues to be objected of a plurality of standard subjects respectively, obtained by the second kind image diagnostic apparatus, which is created so as to be a standard of the second medical image data, and to which second coordinate information to be an index of the alignment is added, and of determining, based on the relative positional relationship, a first transformation matrix for transforming one image data out of the specified second medical image data and the atlas second medical image data into the image data in the coordinate system to which the other image data belongs;

second transformation matrix acquisition step of determining a relative positional relationship between the coordinate system to which the atlas second medical image data belongs and the coordinate system to which the specified first medical image data belongs based on the first coordinate information and the second coordinate information, and of determining, based on the relative positional relationship, a second transformation matrix for transforming one image data out of the atlas second medical image data and the specified first medical image data into the image data in the coordinate system to which the other image data belongs; and specified medical image data alignment step of aligning the specified first medical image data and the specified second medical image data using the first transformation matrix and the second transformation matrix.

A medical image data alignment program according to the present invention is a medical image data alignment program for causing a computer to execute processing for aligning specified first medical image data holding form information of a tissue to be objected of a specified subject, obtained by a first kind image diagnostic apparatus, and specified second medical image data holding function information of the tissue to be objected of the specified subject, obtained by a second kind image diagnostic apparatus, the program causing the computer to execute:

a first coordinate information addition step of adding first coordinate information to be an index for alignment to the specified first medical image data;

a first transformation matrix acquisition step of determining a relative positional relationship between a coordinate system to which the specified second medical image data belongs and a coordinate system to which atlas second medical image data belongs based on the correlation of mutual image signal values of the specified second medical image data and the atlas second medical image data which is created based on a plurality of second medical image data holding function information of tissues to be objected of a plurality of standard subjects respectively, obtained by the second kind image diagnostic apparatus, which is created so as to be a standard of the second medical image data, and to which second coordinate information to be an index of the alignment is added, and of determining, based on the relative positional relationship, a first transformation matrix for transforming one image data out of the specified second medical image data and the atlas second medical image data into the image data in the coordinate system to which the other image data belongs;

second transformation matrix acquisition step of determining a relative positional relationship between the coordinate system to which the atlas second medical image data belongs and the coordinate system to which the specified first medical image data belongs based on the first coordinate information and the second coordinate information, and of determining, based on the relative positional relationship, a second transformation matrix for transforming one image data out of the atlas second medical image data and the specified first medical image data into the image data in the coordinate system to which the other image data belongs; and specified medical image data alignment step of aligning the specified first medical image data and the specified second medical image data using the first transformation matrix and the second transformation matrix.

According to the medical image data alignment apparatus, method and program of the present invention, alignment of the specified first medical image data and the specified second medical image data is performed in steps via the atlas second medical image data, whereby the following functional effects are exhibited.

The atlas second medical image data is data which is created based on a plurality of second medical image data holding function information of a tissue to be objected of a plurality of standard subjects respectively so as to be the standard of the second medical image data, and to which the second coordinate information to be the index of alignment is added, and can be provided after sufficient accuracy verification in advance.

According to the present invention, operation steps to be executed in the medical work site include: a step of adding the first coordinate information to be the index of alignment, to the specified first medical image data; a step of aligning the specified second medical image data and the atlas second medical image data (determining the first transformation matrix); a step of aligning the atlas second medical image data and the specified first medical image data (determining second transformation matrix); and a step of aligning the specified first medical image data and the specified second medical image data.

The specified first medical image data holds form information of the tissue to be objected, so it is easy to add the first coordinate information to the specified first medical image data, at high accuracy with sufficient reproducibility. The specified second medical image data and the atlas second medical image data, which are the same kind of data, have high correlation in the image signal values, and the alignment of these image data based on this correlation can be performed in a short time and at high accuracy. The atlas second medical image data and the specified first medical image data, on the other hand, are different kinds of image data from each other, but these image data are aligned based on the first coordinate information added to the first medical image data and the second coordinate information added to the atlas second medical image data, therefore this alignment can be performed in a short time at high accuracy as well. The final alignment of the specified first medical image data and the specified second medical image data can be performed by arithmetic processing using the determined first transformation matrix and the second transformation matrix, therefore this alignment can also be performed in a short time at high accuracy.

Hence according to the medical image data alignment apparatus, method and program of the present invention, different kinds of image data on the tissue to be objected, between the medical image obtained by the first kind image diagnostic apparatus which can generate an image of the form information of the tissue to be objected, and the medical image obtained by the second kind image diagnostic apparatus which can generate an image of the function information of the tissue to be objected, can be aligned in a short time with sufficient accuracy and reproducibility.

DESCRIPTION OF THE PREFERRED EMBODIMENTS

Embodiments of the present invention will now be described in detail with reference to the above mentioned drawings. First, a medical image data alignment apparatus according to an embodiment of the present invention will be described with reference to FIG. 1 and FIG. 2.

Figure 1:
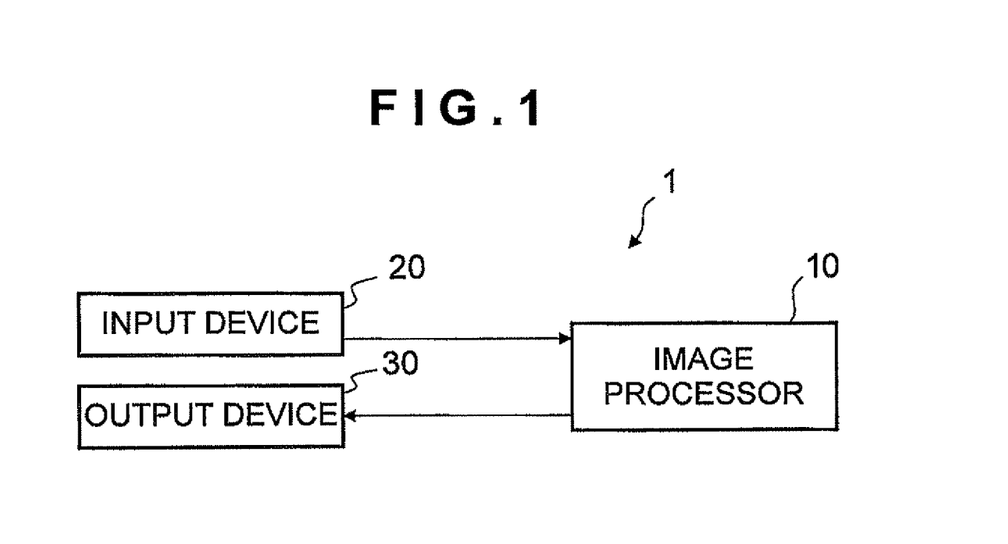
FIG. 1 is a diagram depicting a general configuration of a medical image data alignment apparatus according to an embodiment.

The medical image data alignment apparatus 1 shown in FIG. 1 aligns specified first medical image data holding form information of a tissue to be objected of a specified subject (specified patient) obtained by a first kind image diagnostic apparatus, and specified second medical image data holding function information of the tissue to be objected of the specified subject, obtained by a second kind image diagnostic apparatus, and has an image processor 10 which is a computer or the like, an input device 20 such as a mouse and keyboard, and an output device 30 which is an image display device, for example.

In the present embodiment, a case when the first kind image diagnostic apparatus is an X-ray CT apparatus, the second kind image diagnostic apparatus is a SPECT apparatus, and the tissue to be objected is a heart of a patient who is suspected of having an ischemic heart disease, will be described. In the following description, the specified first medical image data may be called a "patient CT", and the specified second medical image data may be called a "patient SPECT".

Figure 2:
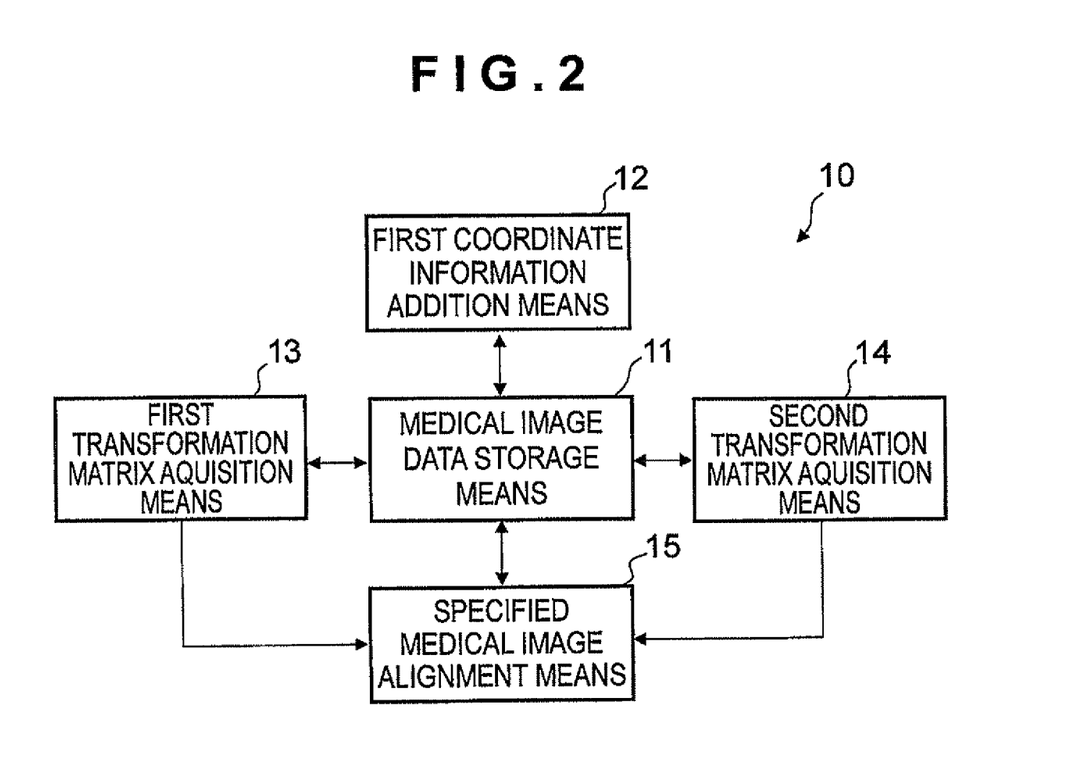
FIG. 2 is a block diagram depicting a configuration of the image processor shown in FIG. 1.

As shown in FIG. 2, the image processor 10 has medical image data storage means 11, first coordinate information addition means 12, first transformation matrix acquisition means 13, second transformation matrix acquisition means 14 and specified medical image alignment means 15. These means, which are conceptually shown here, are constituted by a CPU which executes various arithmetic processing, storage devices such as a hard disks, and control programs (including the medical image data alignment program according to an embodiment of the present invention) stored in the storage devices, for example.

The medical image data storage means 11 stores a patient CT holding anatomical form information of a heart of a specified subject, obtained by the X-ray CT apparatus, a patient SPECT holding function information, such as blood flow of the heart of a specified subject, obtained by a SPECT apparatus, and atlas second medical image data (may be called "atlas data" hereinbelow), which is based on a plurality of second medical image data (SPECT image data) holding function information of hearts of a plurality of standard subjects (a plurality of standard patients), obtained by the SPECT apparatus and is created to be the standard of the second medical image data, and to which second coordinate information to be the index of alignment is added.

The first coordinate information addition means 12 adds first coordinate information to be the index of alignment to the patient CT.

The first transformation matrix acquisition means 13 determines the relative positional relationship between the coordinate system to which the patient SPECT belongs and the coordinate system to which the atlas data belongs, based on the correlation of the mutual image signal values (SPECT values) of the patient SPECT and the atlas data, and determines a first transformation matrix for transforming one image data, out of the patient SPECT and the atlas data, into image data in the coordinate system to which the other image data belongs, based on the above mentioned relative positional relationship.

The second transformation matrix acquisition means 14 determines the relative positional relationship between the coordinate system to which the atlas data belongs and the coordinate system to which the patient CT belongs, based on the first coordinate information and the second coordinate information, and determines a second transformation matrix for transforming one image data, out of the atlas data and the patient CT, into image data in the coordinate system to which the other image data belongs, based on the above mentioned relative positional relationship.

The specified medical image alignment means 15 aligns the patient CT and the patient SPECT using the first transformation matrix and the second transformation matrix.

Now a medical image data alignment method according to an embodiment of the present invention will be described with reference to FIG. 3 to FIG. 8. The basic procedure of the medical image data alignment method according to the present embodiment is executed by the above mentioned medical image data alignment apparatus 1, which is operated according to the medical image data alignment program according to an embodiment of the present invention.

Figure 4:
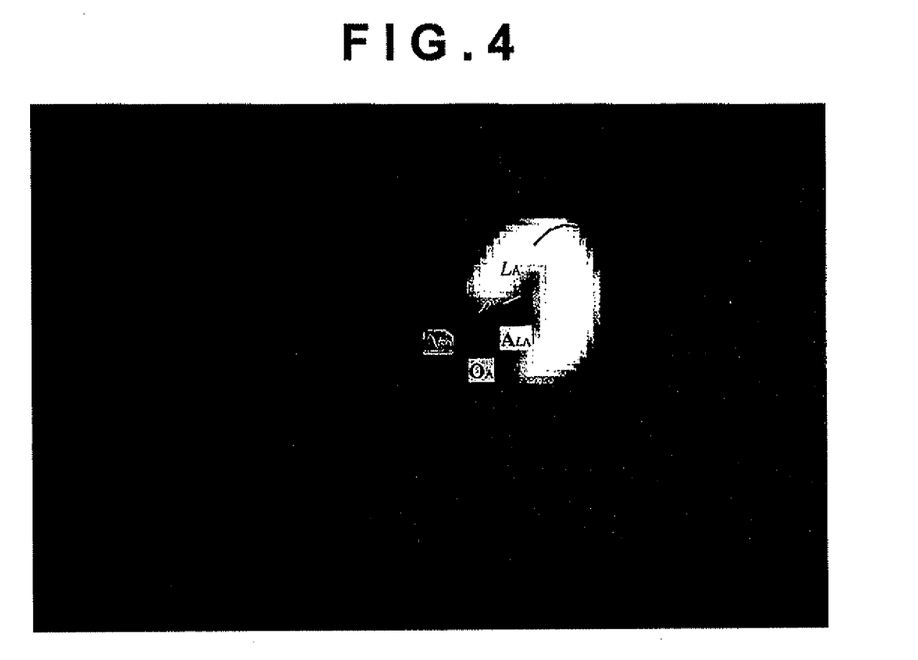
FIG. 4 is an image showing an example of an atlas second medical image data.
Figure 5:
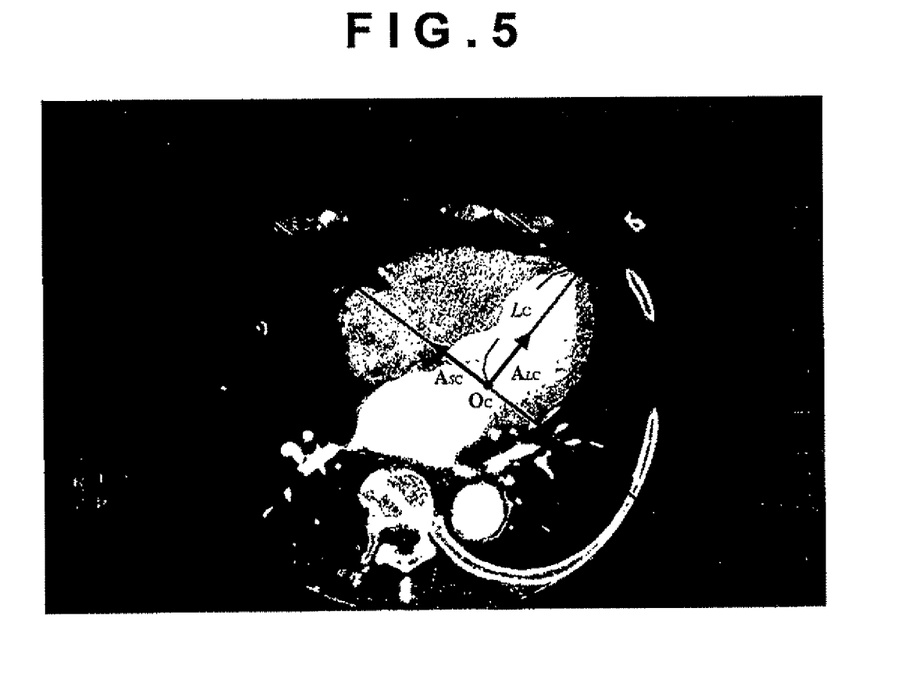
FIG. 5 is an image showing an example of a specified first medical image data to which first coordinate information is added.

First, atlas data (see FIG. 4), which is created in advance before executing the basic alignment procedure, will be described. The atlas data shown in FIG. 4 is created by aligning the SPECT image data of hearts of a plurality of patients of which ischemia is relatively low, based on the correlation of the respective image signal values (SPECT value in each voxel), and averaging the image signal values in the portion which overlapped as a result of alignment. In the present embodiment, a rigid registration method is used as an alignment method in this case, but another method, such as non-rigid registration, can also be used.

In this atlas data, second coordinate information to be an index of alignment, specifically each information on a unit vector $A_{LA}$ of the left ventricle in the long axis direction, a unit vector $A_{SA}$ thereof in the short axis direction, a basic point position (heart base) $O_A$ of the left ventricle, and the length $L_A$ of the left ventricle, is added.

The second coordinate information is determined by the following procedure, for example. First, the CT image data (hereafter called "standard patient CT", not illustrated) of the heart of the patient on which the atlas data was based is imaged, and in this standard patient CT, each information of the unit vector $A'_{LC}$ of the left ventricle in the long axis direction, unit vector $A'_{SC}$ thereof in the short axis direction, basic point position (heart base) $O'_C$ of the left ventricle, and the length $L'_C$ of the left ventricle, is determined. Then this standard patient CT and the atlas data are aligned, and the transformation matrix $T_A$ for transforming the standard patient CT into data in the coordinate system, to which the atlas data belongs, is determined. Using this transformation matrix $T_A$, the above mentioned second coordinate information is determined (see the following Expressions (1) to (4)). The extraction of each information of the unit vector $A'_{LC}$, $A'_{SC}$, basic position $O'_C$ of the left ventricle and the length $L'_C$ of the left ventricle from the standard patient CT, and the alignment of the standard patient CT and the atlas data, are manually performed by an expert skilled in this operation, and the accuracy thereof is sufficiently verified, but these operations may be performed automatically.

$$O_A = T_A O'_C \quad (1)$$

$$A_{LA} = T_A A'_{LC} \quad (2)$$

$$A_{SA} = T_A A'_{SC} \quad (3)$$

$$L_A = L'_C \quad (4)$$

Now a basic procedure of the medical image data alignment method according to the present embodiment will be described.

Figure 3:
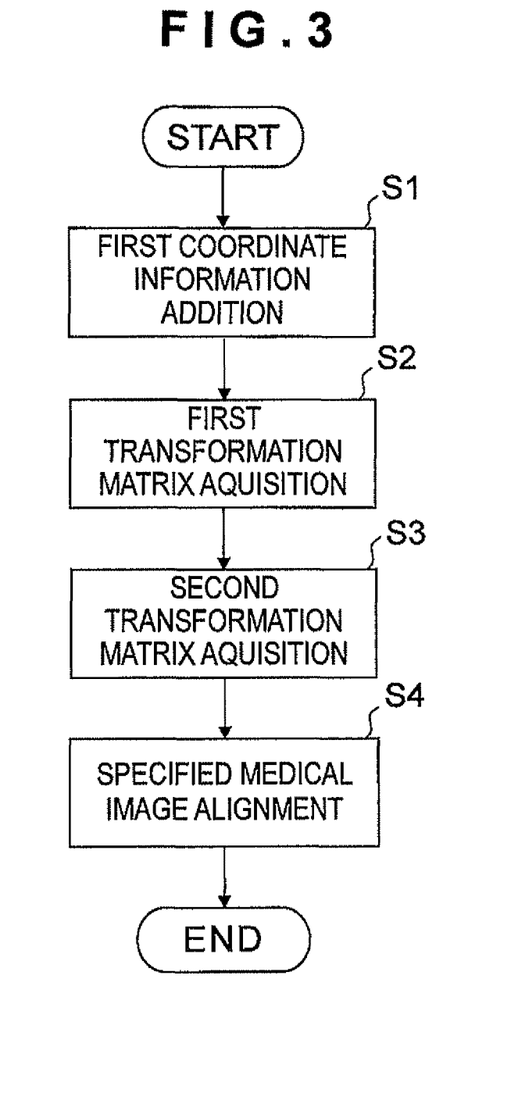
FIG. 3 is a flow chart depicting a medical image data alignment method according to an embodiment.

<1> The first coordinate information to be the index of alignment is added to the patient CT (first coordinate information addition step, see step S1 in FIG. 3). In the present embodiment, each information on the unit vector $A_{LC}$ of the left ventricle in the long axis direction, unit vector $A_{SC}$ thereof in the short axis direction, basic point position (heart base) $O_C$ of the left: ventricle, and length k of the left ventricle, is added as the first coordinate information (see FIG. 5). The first coordinate information to be added is calculated by an operator, such as a physician, using the first coordinate information addition means 12, while viewing the patient CT displayed on the output device 30, based on predetermined information which was input to the image processor 10 via the input device 20 (each information on the left ventricle in the long axis and short axis, heart base and heart tip of the left ventricle). According to the present embodiment, the cardiac muscle of the left ventricle can be extracted by segmentation of the left ventricle in the patient CT when the first coordinate information is added (a conventionally known method can be used for the segmentation), but the segmentation result is not used for the later mentioned alignment processing, and therefore does not influence the accuracy of the alignment.

Figure 6:
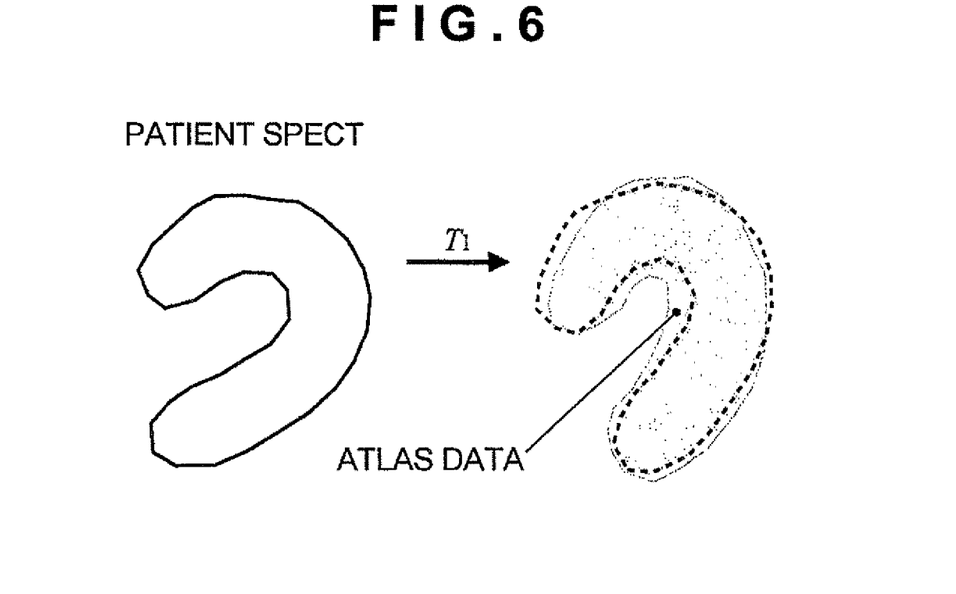
FIG. 6 is a diagram depicting an outline of a method for determining a first transformation matrix.

<2> The relative positional relationship between the coordinate system to which the patient SPECT belongs and the coordinate system to which the atlas data belongs is determined based on the correlation of the mutual image signal values (SPECT values) of the patient SPECT and the atlas data, and the first transformation matrix $T_1$ for transforming the patient SPECT into the image data in the coordinate system to which the atlas data belongs, based on the relative positional relationship (first transformation matrix acquisition step, step S2 in FIG. 3, see FIG. 6). According to the present embodiment, the patient SPECT is aligned with the atlas data using a rigid registration method, and the first transformation matrix $T_1$ is calculated by the first transformation matrix acquisition means 13 based on the information obtained by the alignment. For the alignment evaluation function, a normalized mutual information amount is used.

Figure 7:
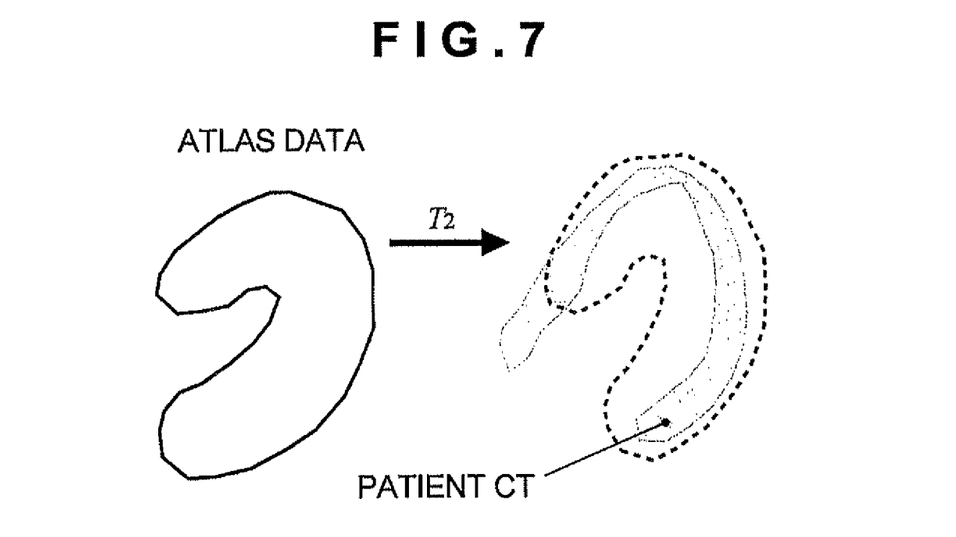
FIG. 7 is a diagram depicting an outline of a method for determining a second transformation matrix.

<3> The relative positional relationship between the coordinate system to which atlas data belongs and the coordinate system to which the patient CT belongs is determined based on the first coordinate information added to the patient CT and the second coordinate information added to the atlas data, and the second transformation matrix $T_2$ for transforming the atlas data into the image data in the coordinate system to which the patient CT belongs, is determined based on the relative positional relationship (second transformation matrix acquisition step, step S3 in FIG. 3, see FIG. 7). In the present embodiment, the second transformation matrix $T_2$ is calculated by the second transformation matrix acquisition means 14 according to the following procedure in more concrete terms.

First, parallel translation $t_1$, by which the basic point position $O_A$ of the left ventricle in the atlas data overlaps with the basic point position $O_C$ of the left ventricle in the patient CT, is calculated (see the following Expression (5)).

$$t_1 = O_A - O_C \qquad (5)$$

Then a rotation matrix $R_1$, by which the unit vector $A_{LA}$ of the left ventricle in the long axis direction and the unit vector $A_{SA}$ thereof in the short axis direction in the atlas data overlap with the unit vector $A_{LC}$ of the left ventricle in the long axis direction and the unit vector $A_{SC}$ thereof in the short axis direction in the patient CT respectively, is calculated (see the following Expression (6)).

$$R_1 = R_{12} R_{11} \qquad (6)$$

(where $R_{11}$ is a matrix represented by the following Expression (A) and $R_{12}$ is a matrix represented by the following Expression (B).)

$$R_{11} = \begin{pmatrix} e_{11}^2(1-C_1)+C_1 & e_{11}e_{12}(1-C_1)-e_{13}S_1 & e_{11}e_{13}(1-C_1)+e_{12}S_1 \\ e_{11}e_{12}(1-C_1)+e_{13}S_1 & e_{12}^2(1-C_1)+C_1 & e_{12}e_{13}(1-C_1)-e_{11}S_1 \\ e_{11}e_{13}(1-C_1)-e_{12}S_1 & e_{12}e_{13}(1-C_1)+e_{11}S_1 & e_{13}^2(1-C_1)+C_1 \end{pmatrix} \text{ where} \qquad (A)$$

$$e_1 = \begin{pmatrix} e_{11} \\ e_{12} \\ e_{13} \end{pmatrix} = A_{LC} \times A_{LA}, \; C_1 = A_{LC} \cdot A_{LA}, \; S_1 = \sqrt{1-C_1^2}$$

$$R_{12} = \begin{pmatrix} e_{21}^2(1-C_2)+C_1 & e_{21}e_{22}(1-C_2)-e_{23}S_2 & e_{21}e_{23}(1-C_2)+e_{22}S_2 \\ e_{21}e_{22}(1-C_2)+e_{23}S_2 & e_{22}^2(1-C_2)+C_2 & e_{22}e_{23}(1-C_2)-e_{21}S_2 \\ e_{21}e_{23}(1-C_2)-e_{22}S_2 & e_{22}e_{23}(1-C_2)+e_{21}S_2 & e_{23}^2(1-C_2)+C_2 \end{pmatrix} \text{ where} \qquad (B)$$

$$e_2 = \begin{pmatrix} e_{21} \\ e_{22} \\ e_{23} \end{pmatrix} = A_{LC}, \; C_2 = A_{SC} \cdot (R_{11} A_{SA}), \; S_2 = \sqrt{1-C_2^2}$$

Then a parallel translation $t_2$, by which the heart tip in the atlas data overlaps with the heart tip in the patient CT, is calculated considering the difference among individuals (mismatch of the lengths of left ventricles) between the atlas data and patient CT (see the following Expression (7)).

$$t_2 = A_{LC}(L_A - L_C) \qquad (7)$$

Finally integrating the Expressions (5) to (7), the second transformation matrix $T_2$ is calculated (see the following Expression (8)).

$$T_2 = (R_1 | t_1 + t_2) \qquad (8)$$

Figure 8:
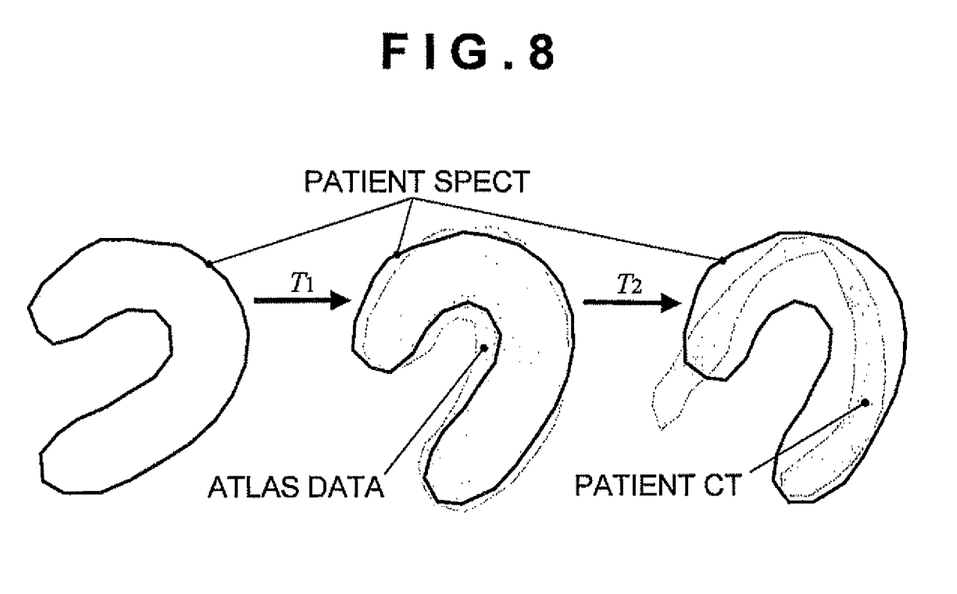
FIG. 8 is a diagram depicting an outline of an alignment of specified first medical image data and specified second medical image data.

<4> The patient CT and the patient SPECT are aligned using the determined first transformation matrix $T_1$ and the second transformation matrix $T_2$ (specified medical image alignment step, step S4 in FIG. 3, see FIG. 8). According to the present embodiment, alignment of the patient SPECT to the patient CT is executed by the specified medical image alignment means 15 by sequentially applying the first transformation matrix $T_1$ and the second transformation matrix $T_2$ to the patient SPECT.

According to the present embodiment, the patient CT and the patient SPECT are aligned, and then a CT/SPECT integrated image, in which the patient CT and the patient SPECT are integrated, (the image in which the SPECT values are mapped on the surface of the segment left ventricle) is created, and displayed on the output device 30.

As an experiment to verify the usability of the above described invention, misalignment was generated using random numbers in the pre-aligned patient CT and patient SPECT, and the misalignment was returned to the original state by the present invention. For comparison, a specialist performed the alignment, and the difference of this result from the alignment result by the present invention was calculated as an error. As a result, this error was confined to a narrow range, and the usability of the present invention was confirmed.

An embodiment of the present invention was described, but the present invention is not limited to the embodiment, for numerous modifications can be made.

For example, in the above mentioned embodiment, a case when the first kind image diagnostic apparatus is the X-ray CT apparatus, the second kind image diagnostic apparatus is the SPECT apparatus, and the tissue to be objected is a heart, was described, but the present invention can also be usefully applied to the case when the first kind image diagnostic apparatus is an MRI apparatus. There is no particular difficulty in applying the present invention to image data obtained by the MRI apparatus, and the above mentioned procedure of the present invention can be applied in a similar manner.

The tissue to be objected can be such an organ as a pancreas, kidney, spleen, liver, brain and lung, or such a biotissue as a tumor, instead of the heart. There is no particular difficulty in applying the present invention to the case when another tissue is a tissue to be objected, and the above mentioned procedure of the present invention can be applied in a similar manner regardless the type of the tissue to be objected.

What is claimed is:

1. A medical image data alignment apparatus for aligning specified first medical image data holding form information of a tissue to be objected of a specified subject, obtained by a first kind image diagnostic apparatus, and specified second medical image data holding function information of the tissue to be objected of the specified subject, obtained by a second kind image diagnostic apparatus, comprising:

medical image data storage means for storing the specified first medical image data, the specified second medical image data, and atlas second medical image data which is created based on a plurality of second medical image data holding function information of tissues to be objected of a plurality of standard subjects respectively, obtained by the second kind image diagnostic apparatus, which is created so as to be a standard of the second medical image data, and to which second coordinate information to be an index of the alignment is added;

first coordinate information addition means for adding first coordinate information to be an index for alignment to the specified first medical image data;

first transformation matrix acquisition means for determining a relative positional relationship between a coordinate system to which the specified second medical image data belongs and a coordinate system to which the atlas second medical image data belongs based on the correlation of mutual image signal values of the specified second medical image data and the atlas second medical image data, and for determining, based on the relative positional relationship, a first transformation matrix for transforming one image data out of the specified second medical image data and the atlas second medical image data into the image data in the coordinate system to which the other image data belongs;

second transformation matrix acquisition means for determining a relative positional relationship between the coordinate system to which the atlas second medical image data belongs and the coordinate system to which the specified first medical image data belongs based on the first coordinate information and the second coordinate information, and for determining, based on the relative positional relationship, a second transformation matrix for transforming one image data out of the atlas second medical image data and the specified first medical image data into the image data in the coordinate system to which the other image data belongs; and specified medical image data alignment means for aligning the specified first medical image data and the specified second medical image data using the first transformation matrix and the second transformation matrix.

2. The medical image data alignment apparatus according to claim 1, wherein the atlas second medical image data is created by mutually aligning the plurality of second medical image data based on the correlation of respective image signal values thereof and averaging the image signal values in portions which are overlapped with each other by the alignment.

3. The medical image data alignment apparatus according to claim 1, wherein the first coordinate information and the second coordinate information are constituted by unit vectors in a long axis direction and a short axis direction of the specified tissue to be objected, a basic point position of the specified tissue to be objected, and a predetermined length of the specified tissue to be objected.

4. The medical image data alignment apparatus according to claim 1, wherein the first kind image diagnostic apparatus is a CT apparatus or an MRI apparatus, and the second kind image diagnostic apparatus is a SPECT apparatus.

5. The medical image data alignment apparatus according to claim 1, wherein the tissue to be objected is a heart.

6. A medical image data alignment method for aligning specified first medical image data holding form information of a tissue to be objected of a specified subject, obtained by a first kind image diagnostic apparatus, and specified second medical image data holding function information of the tissue to be objected of the specified subject, obtained by a second kind image diagnostic apparatus, comprising the steps of:

adding first coordinate information to be an index for alignment to the specified first medical image data;

determining a relative positional relationship between a coordinate system to which the specified second medical image data belongs and a coordinate system to which atlas second medical image data belongs based on the correlation of mutual image signal values of the specified second medical image data and the atlas second medical image data which is created based on a plurality of second medical image data holding function information of tissues to be objected of a plurality of standard subjects respectively, obtained by the second kind image diagnostic apparatus, which is created so as to be a standard of the second medical image data, and to which second coordinate information to be an index of the alignment is added, and determining, based on the relative positional relationship, a first transformation matrix for transforming one image data out of the specified second medical image data and the atlas second medical image data into the image data in the coordinate system to which the other image data belongs;

determining a relative positional relationship between the coordinate system to which the atlas second medical image data belongs and the coordinate system to which the specified first medical image data belongs based on the first coordinate information and the second coordinate information, and determining, based on the relative positional relationship, a second transformation matrix for transforming one image data out of the atlas second medical image data and the specified first medical image data into the image data in the coordinate system to which the other image data belongs; and aligning the specified first medical image data and the specified second medical image data using the first transformation matrix and the second transformation matrix.

7. A non-transitory computer readable medium storing medical image data alignment program for causing a computer to execute processing for aligning specified first medical image data holding form information of a tissue to be objected of a specified subject, obtained by a first kind image diagnostic apparatus, and specified second medical image data holding function information of the tissue to be objected of the specified subject, obtained by a second kind image diagnostic apparatus, the program causing the computer to execute the steps of:

adding first coordinate information to be an index for alignment to the specified first medical image data;

determining a relative positional relationship between a coordinate system to which the specified second medical image data belongs and a coordinate system to which atlas second medical image data belongs based on the correlation of mutual image signal values of the specified second medical image data and the atlas second medical image data which is created based on a plurality of second medical image data holding function information of tissues to be objected of a plurality of standard subjects respectively, obtained by the second kind image diagnostic apparatus, which is created so as to be a standard of the second medical image data, and to which second coordinate information to be an index of the alignment is added, and determining, based on the relative positional relationship, a first transformation matrix for transforming one image data out of the specified second medical image data and the atlas second medical image data into the image data in the coordinate system to which the other image data belongs;

determining a relative positional relationship between the coordinate system to which the atlas second medical image data belongs and the coordinate system to which the specified first medical image data belongs based on the first coordinate information and the second coordinate information, and determining, based on the relative positional relationship, a second transformation matrix for transforming one image data out of the atlas second medical image data and the specified first medical image data into the image data in the coordinate system to which the other image data belongs; and aligning the specified first medical image data and the specified second medical image data using the first transformation matrix and the second transformation matrix.

8. The medical image data alignment apparatus according to claim 2, wherein the first kind image diagnostic apparatus is a CT apparatus or an MRI apparatus, and the second kind image diagnostic apparatus is a SPECT apparatus.

9. The medical image data alignment apparatus according to claim 3, wherein the first kind image diagnostic apparatus is a CT apparatus or an MRI apparatus, and the second kind image diagnostic apparatus is a SPECT apparatus.

* * * * *